(12) United States Patent
Karasina

(10) Patent No.: US 10,383,697 B2
(45) Date of Patent: Aug. 20, 2019

(54) SURGICAL ITEM COUNTING STATION AND METHOD OF USE

(71) Applicant: Svetlana Karasina, Basking Ridge, NJ (US)

(72) Inventor: Svetlana Karasina, Basking Ridge, NJ (US)

(*) Notice: Subject to any disclaimer, the term of this patent is extended or adjusted under 35 U.S.C. 154(b) by 77 days.

(21) Appl. No.: 15/457,311

(22) Filed: Mar. 13, 2017

(65) Prior Publication Data

US 2017/0258547 A1   Sep. 14, 2017

Related U.S. Application Data

(60) Provisional application No. 62/307,526, filed on Mar. 13, 2016.

(51) Int. Cl.

| A61B 50/36 | (2016.01) |
|---|---|
| A61B 50/37 | (2016.01) |
| A61B 50/26 | (2016.01) |
| A61B 90/00 | (2016.01) |
| F16B 1/00 | (2006.01) |
| A61B 50/30 | (2016.01) |

(52) U.S. Cl.
CPC .............. *A61B 90/08* (2016.02); *A61B 50/26* (2016.02); *A61B 50/36* (2016.02); *A61B 50/37* (2016.02); *F16B 1/00* (2013.01); *A61B 2050/314* (2016.02); *A61B 2050/375* (2016.02); *A61B 2090/0804* (2016.02); *F16B 2001/0035* (2013.01)

(58) Field of Classification Search
CPC . F16B 2001/0035; A61B 50/26; A61B 50/36; A61B 90/08; A61B 50/37; A61B 50/10–18; A61B 50/24; A61B 50/33; A61B 2050/155; A61B 2050/375; A61G 11/00–009; A61G 12/001; A61G 12/002; A61G 12/007; A61G 12/008
USPC ......................................... 361/807, 809, 810
See application file for complete search history.

(56) References Cited

U.S. PATENT DOCUMENTS

| 4,234,086 A | 11/1980 | Dorton |
|---|---|---|
| 4,361,231 A | 11/1982 | Patience |
| 4,422,548 A | 12/1983 | Cheesman et al. |

(Continued)

FOREIGN PATENT DOCUMENTS

CA   1161327   1/1984

*Primary Examiner* — Thaddeus B Cox
(74) *Attorney, Agent, or Firm* — LaCroix IP, LLC; Margaret A. LaCroix

(57) ABSTRACT

A surgical item counting station for providing organization and efficiency in counting items and communicating information. The surgical item counting station comprises a top plate having a diameter forming a table top surface and being adjacent and perpendicular to a display screen mounted on an adjustable column mounted on a base terminating at feet. The display screen is adapted to receive and display information about at least one item and general communications. A shelf having a substantially equal diameter to the top plate and being located below and in parallel to the top plate is provided. The shelf includes shelf side walls with a mounting means adapted for mounting at least one container device below the top plate. Preferably the container device is a sponge count bag. Preferably the shelf is a rotational shelf while the top plate or table top is non-rotational.

17 Claims, 11 Drawing Sheets

(56) References Cited

U.S. PATENT DOCUMENTS

| | | | |
|---|---|---|---|
| 4,428,488 A | 1/1984 | Mcavinn et al. | |
| 6,102,497 A * | 8/2000 | Ehr | A61G 12/001 |
| | | | 280/47.35 |
| 6,607,170 B1 | 8/2003 | Hoftman | |
| 8,371,448 B1 | 2/2013 | Reaux | |
| 8,544,660 B2 | 10/2013 | Foley | |
| 9,198,727 B1 * | 12/2015 | Samuels | A61F 15/001 |
| 2003/0235029 A1 * | 12/2003 | Doherty | G06F 1/1632 |
| | | | 361/679.27 |
| 2005/0075564 A1 | 4/2005 | Ballard | |
| 2008/0029416 A1 | 2/2008 | Paxton | |
| 2009/0216204 A1 * | 8/2009 | Bhavaraju | A61M 35/00 |
| | | | 604/290 |
| 2013/0193282 A1 * | 8/2013 | Brehm | F16M 13/022 |
| | | | 248/125.7 |
| 2014/0138925 A1 * | 5/2014 | Ono | B62B 3/02 |
| | | | 280/35 |
| 2014/0216305 A1 * | 8/2014 | Hodges | A61B 19/0248 |
| | | | 108/3 |
| 2016/0262843 A1 | 9/2016 | Sellers | |

* cited by examiner

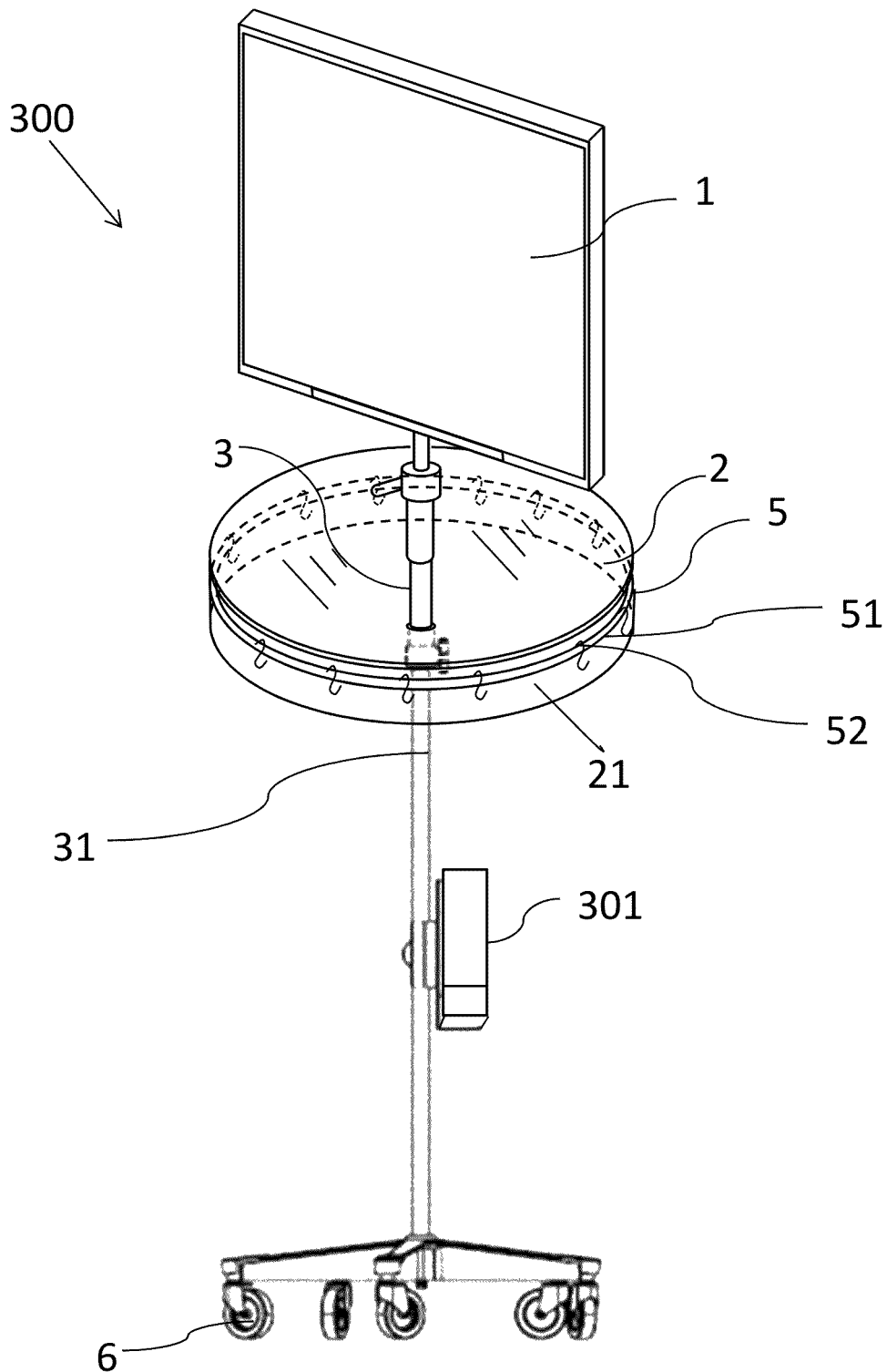

SURGICAL ITEM COUNTING STATION AND METHOD OF USE

CROSS-REFERENCE TO RELATED APPLICATIONS

This is a Nonprovisional Patent Application claims the benefit of U.S. Provisional Application No. 62/307,526 entitled "Count Stand" filed on Mar. 13, 2016, the disclosure of which is hereby incorporated in its entirety by reference thereto.

FIELD OF THE INVENTION

The present invention relates to medical devices for storing and keeping an account of objects.

DESCRIPTION OF THE PRIOR ART

While there are numerous caddies and tables on which to place surgical instruments and other objects, such as sponges, there is no definitive method to account for the object. All too often sponges, and even instruments, have been left inside of a patient during surgery because they are not methodically accounted for during operation procedures. The term Retained Surgical Items (RSI) generally refers to surgical items, such as tools, materials and/or sponges, inadvertently left in a patient's body during a surgical operation. RSI is considered a significant surgical patient safety problem. Evidence suggests that one (1) in ten thousand (10,000) operations will result in a RSI, with an estimated cost of two-hundred thousand dollars ($200,000) per incident, with an estimated 10-15% of these issues resulting from count error. While the lay person can appreciate the shock of these incidents, one should realize also that RSI are considered a "never" (sentinel) event, or sentinel event. Sentinel events are defined by The Joint Commission (TJC) as any unanticipated event in a healthcare setting resulting in death or serious physical or psychological injury to a patient or patients, not related to the natural course of the patient's illness. Such events are reportable to government and regulating agencies. Misplaced objects can result in: wrong site procedure; clinical deterioration; surgical site infections; and/or RSI.

It is critical for surgical items, such as needles and sponges, to be fully accounted for during surgical procedures to prevent RSI events. According to the Guideline Summary for Prevention of RSI by the Association of periOperative Registered Nurses "items being counted should be viewed concurrently and counted audibly by two individuals, one of whom should be the RN". "Guideline Summary: Prevention of Retained Surgical Items", AORN Journal, July 2016, Vol. 104, No. 1, pg. 49-53. The person who is "scrubbed in" is responsible for counting sterile items on the sterile field, and the other for recording the non-sterile items that have been removed from the sterile field. The counts are written on a white board/other communication board typically located away from the operative field. Owing to the location of the white board/communication board, one nurse must be in transit within the operating room to record the surgical item count. Other practices at some facilities rely on a clip-board with a sheet for counting as opposed to a white board/communication board. Nonetheless, standardized count records and the placement of a chalk or whiteboard in all operating rooms for annotation, and the establishment of a specific label in place for counting and placing each surgical sponge/item has been recommended by various research studies. Freitas, et al., "Surgical count process for prevention of retained surgical items: an integrative review", Journal of Clinical Nursing, 25, 2016, 1835-1847, pg. 1843. This process opens up an opportunity for communication errors, other surgical equipment/supplies/personnel obstructing direct view of items being counted by both personnel and overall increases the risk of human factors affecting the accuracy of the counts. Current evidence suggests that almost 88% of RSI cases had a "correct" final count, further highlighting the challenges behind a de-centralized counting system and human factors that drive the RSI as among the "most frequently reported sentinel events for the past 10 years and comprise half the malpractice settlements for surgical 'never events'". STEELMAN, et al., "The Hidden Costs of Reconciling Surgical Sponge Counts", AORN Journal, November 2015, Vol. 102, No. 5, 2015, pg. 498-505, pg. 502. Furthermore, walking to and fro within the surgical suite is a practice that has been associated with increased air turbulence and therefore increased risk of infections. At the conclusion of the surgical procedure, and prior to suturing, full accounting the surgical and sponge implements must be finalized.

To counter RSI event various counting devices, particularly for sponges and needles, have been provided. Radio frequency (RF) or electromagnetic wave frequency technologies have been employed in attempting to avoid RSI of sponges, for example. In these types of devices, typically a conductor is embedded within a surgical sponge/or item, whereupon upon removal from the patient and placed within a receptacle current radiates off the conductor of the sponge, and the signal is read and recorded for counting. However, RF technology in item counting is still not widely implemented throughout surgical procedures, and does not assist for items that do not contain the embedded conductors, and therefore manual item count of sponges and needles, for example, is still customary.

Manual sponge counting devices heretofore disclosed and utilized typically provide receptacles and/or containment sleeves or pouches whereupon soiled surgical items, such as sponges and needles, are disposed. While items are removed from the patient, the field nurse must physically record the count, typically on a white board/display board frequently located across the room away from the surgical locus. As discussed hereinabove, manual count recordation at the separately located display board often leads to communication errors and air turbulence in the operating room as the recording/field nurse moves to and fro increasing patient infection risks.

Despite the use these surgical item counting devices, RSI events, especially those involving sponges and needles, are still prevalent and represent a significant problem during surgical procedures. Consequently, the risk of miscount of surgical item recovery during surgical procedures resulting in RSI still represents a significant problem.

Based on the foregoing, there exists a need in the art for a device and/or method that provides an organized system for disposing of and recording surgical item collection during surgical procedures. Furthermore, there is a need in the art for a item counting device and/or method that improves efficiency, decreases duration of counts, offers a centralized counting location, decreases unnecessary movement, promotes safety, and decreases human factor errors.

SUMMARY OF THE INVENTION

The subject invention provides a central count station for sponges, medication and small items in conjunction with a communication board. A surgical item counting station and method of use is provided that improves efficiency, decreases duration of counts, offers a centralized counting location, decreases unnecessary movement, promotes safety, and decreases human factor errors. A three-dimensional geometric device in a preferred modality is provided, that is on wheels and around the outwardly facing vertical side of which are suspended a plurality of containers and the horizontal top of which is a flat surface often illuminated by a light, often having a raised edge to prevent objects from sliding from the surface and falling to the floor, and on top of which is an electronic or non-electronic screen to display information about the items used with and stored within this invention. A multi-utility flat table top surface is provided for intra-operative supplies and medications. The count station is preferably composed of surgical stainless steel, is compact, mobile and stable, and includes a rotational shelf that enables mounting or hanging of a plurality of standard sponge count bags. Preferably, about one (1) to ten (10) sponge count bags can be mounted on the count station. More preferably, three (3) to six (6) sponge count bags can be mounted on the count station. Most preferably, at least five sponge count bags can be mounted on the count station. The number of sponge count bags capable of being mounted on the station is in proportion to the number of side walls and/or the size of the side walls of the shelf. Preferably, at least one side wall of the shelf remains open without mounting means for mounting a sponge count bag, which wall is preferably aligned with the front face of the display board/communication screen. The subject count station decreases human factor errors, removes the need to copy counts and eliminates travel from the sterile field to the count board, while facilitating team communication and decreasing duration of counts.

In one aspect of the invention a surgical item counting station is provided. The surgical item counting station provides organization and efficiency in counting items and communicating information. The surgical item counting station comprises a top plate having a diameter forming a table top surface and being adjacent and perpendicular to a display screen mounted on an adjustable column mounted on a base terminating at feet. The display screen is adapted to receive and display information about at least one item and general communications. A shelf having a substantially equal diameter to the top plate and being located below and in parallel to the top plate is provided. The shelf includes shelf side walls with a mounting means adapted for mounting at least one container device below the top plate. Preferably the container device is a sponge count bag. Preferably the shelf is a rotational shelf while the top plate or table top is non-rotational.

Another aspect of the invention provides a surgical item counting station, comprising a top plate having a diameter forming a table top surface and being adjacent and perpendicular to a display screen mounted on an adjustable column mounted on a base terminating at feet. The display screen being adapted to receive and display information about at least one item and general communications. A rotational shelf is provided having a substantially equal diameter to the top plate and being located below and in parallel to the top plate. The rotational shelf includes shelf side walls with a mounting means adapted for mounting at least one container device below the top plate, wherein the top plate is non-rotational.

BRIEF DESCRIPTION OF THE DRAWING

The invention will be more fully understood and further advantages will become apparent when reference is had to the following detailed description of the preferred embodiments of the invention and the accompanying drawing, in which:

FIG. 2b is a cross-section view of the mounting bracket of FIG. 2a;

FIG. 3 is a front view of the surgical table of FIG. 1 wherein the standard sponge count bags are not secured on the surgical table;

FIG. 6 shows a side view of the surgical item counting station of FIG. 5a;

FIG. 7 shows a top view of the surgical item counting station of FIG. 5a;

FIG. 8 shows a front view of the surgical item counting station of FIG. 5a;

DETAILED DESCRIPTION OF THE INVENTION

Figure 1:
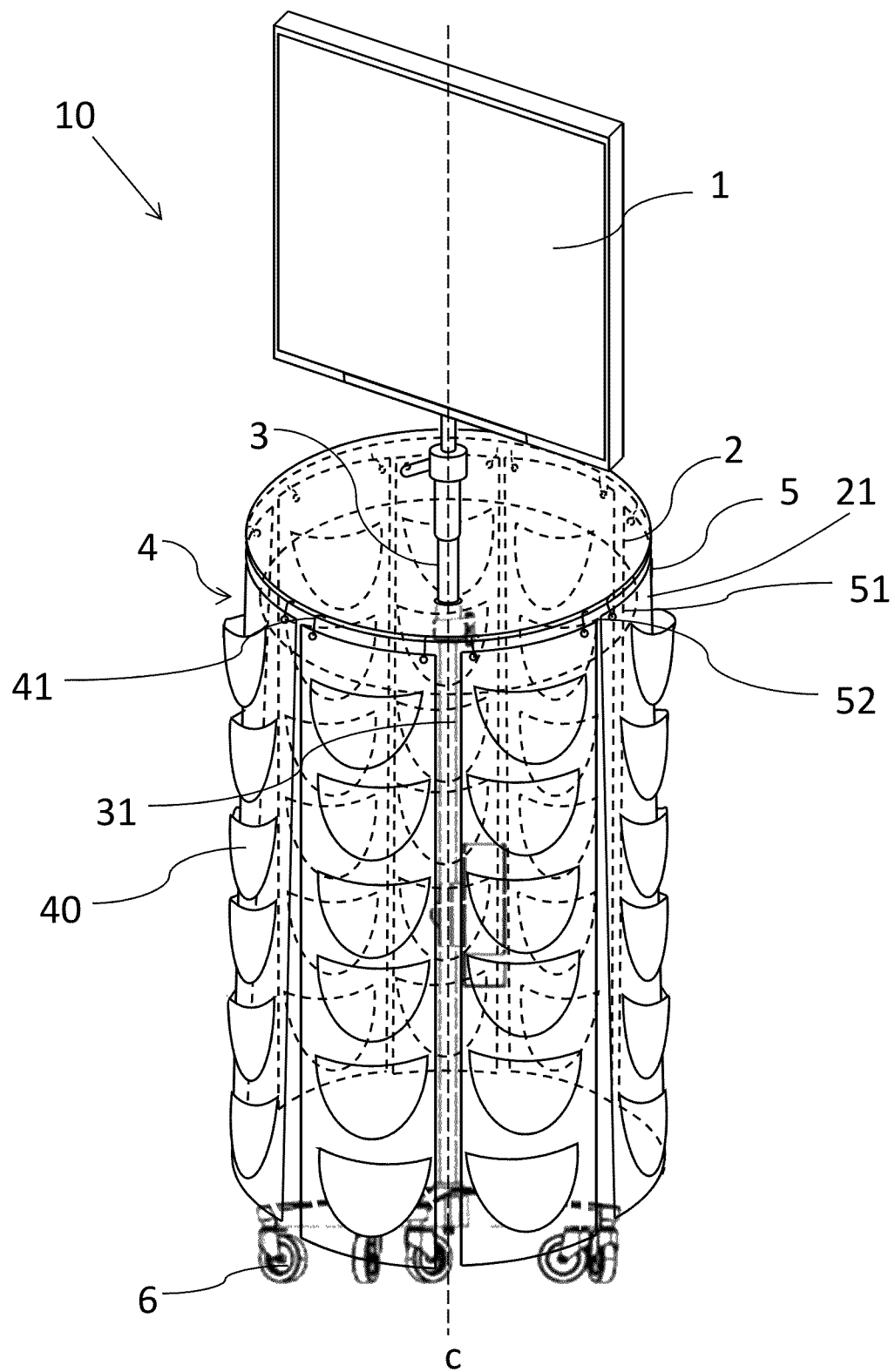
FIG. 1 is a top plan view of an embodiment of the subject surgical item counting station with standard sponge count bags with receptacle pouches secured on the sides of the table.

The subject invention provides a surgical item counting station for organized placement and accounting of surgical items/objects and a visible method for accounting of their whereabouts at all times. Before significant procedures on a patient can go forward, surgical room personnel can be required to check the status of an object on a display screen attached to this invention. It may be called in a more generic sense a "count stand", but in a more formalized setting, a "count station" or a "circulator station" referring to the RN role of a circulator, a RN who is not "scrubbed" and considered non-sterile. Surgical items are herein referred to as items used during a surgical procedure, including for non limiting example, needles, sponges, clamps, needle holders, forceps, scapula, scissors, medications, syringes, specimen containers, sterile and non-sterile supplies, surgical instruments and tools, etc. Though the subject invention herein is discussed as having particular applications regarding surgical sponges and needles, it is to be understood that the subject surgical item counting station can be utilized for a plethora of surgical items.

Several advantageous result from the subject count stand or count station, including: 1) elimination of travel time for circulating nurse from count point to the count board; 2) visually confirm count and writing on the board by scrub nurse and circulating nurse on the spot; 3) improving surgical safety; 4) every team member can see what kind of medication was introduced on the sterile table top surface; 5)

contemporary look; 6) mobile; 7) compact, stable; 8) universal box holder (bracket) is provided on the frame; 9) easy to clean; 10) rotational shelf with clear bags attached for easy display and organization of sponges; 11) universal fit for clear bags; 12) all medication, what was introduced on sterile filed not sitting on the circulation desk (important—antibiotic, Bacitracin, Thrombin, Local medication); 13) compact, round surface the same size as a foot print IV pole; 14) working rotational table for easy and accurate accounting of small surgical items and storing medication; 15) centralized counting location decrease unnecessary movement—decreases duration of count for improved efficiency; 16) promotes safety—decreases human factor errors by eliminating distance and potential barriers to direct observation of the count by two intraoperative personnel; 17) single station for medication and all cont items; and 18) improved quality—facilitates nurse to nurse, tech to tech, and general intraoperative team communication by displaying the count and any pertinent items on the count station visible to the entire team, which facilitates appropriate multidisciplinary clinical decisions; and 19) can be purchased separate; and 20) fits to any existing IV pole.

While this subject invention is appropriate for medical environments, it also may serve for other situations, especially technical ones, as in clean rooms, assembly areas, and various shops. One can itemize the benefits of this invention. For design this invention offers: a) Mid-size, easy to clean, dry-erase board (or an option electronic display, as in a touch screen) for writing and displaying real-time counts; b) a smooth table surface for easy and accurate counting of small surgical items and storing medications; c) (optional) rotational table-top holding clear bags for easy display and organization of sponges; and d) a compact, mobile, stable, contemporary device for easy maneuvering and professional reflection.

In addition, this invention provides advantages including: 1) Improves efficiency; 2) Decreases duration of counts; 3) Coffers a centralized counting location; 4) Decreases unnecessary movement; 5) Promotes safety; 6) Decreases human factor errors by removing the need to copy counts from paper to white board and eliminating barriers from direct observation of counting as well as distance between the two professionals performing the count; 7) Presents a single station for medications and all countable items as well as non-countable items when appropriate (i.e. storing of skin preparation supplies prior to incision or dressing supplies post incision closure); 8) Improves quality of operating room procedure; 9) Facilitates nurse to nurse, tech to tech and any intra-operative personnel report; and 10) Displays a count visible to the entire team and facilitates appropriate multidisciplinary clinical decisions.

This invention is a device adapted to hold objects or items, such as for non limiting example, surgical sponges, in a plurality of containers (i.e. standard sponge count bags) mounted on a plurality of vertical sides or circular surfaces facing outward to a viewer. These sides may be of any material or configuration, as long as they are allowed to be all or in part repositories for objects. The framework on which the storage containers is to be mounted may be three-dimensional cylindrical or polygonal. A planar version is optional, where the frame may be of any shape. For the three-dimensional version, a top horizontal side may be provided that serves as a table often having edges. In one modality the top horizontal side may be illuminated, that illumination being in the form of a lamp mounted so as to shine light toward the top, side or underneath the surface (the face being made of a clear/see-through substance, such as glass or plastic).

Mounted on top of or by the side of the top surface is a device/communication board on which or by which one can record information that normally would pertain to the use of the objects being used around or stored in or with the subject invention, or for general communication. This communication can include, for non limiting example, item count and/or information about the patient (such as recorded vitals, medications, special conditions, and/or general care information). Typically, this is a dry erase board; however it may be an electronic display, such as a computer monitor or light emitting diode-based display screen. Wherein it is an electronic display, the display may be battery operated or provided with a cord for use with a power outlet/source. Optionally, this invention includes one or more power outlets and universal serial board (USB) to power various electronic and other communications devices. Alternatively, at least a portion of the display board may be magnetized. Additionally, the top plate may include at least a portion having a magnet for magnetically securing small metal items, such as drill bits, etc. Preferably, the portion of the top plate that is magnetized is achieved by placing a magnet directly under the top plate so that the top plate is magnetic in the area wherein the magnet is secured underneath. In this manner, the surface of the top plate remains uninterrupted and smooth. Additionally, the back of the display board (i.e. opposite from the face of the display board or writing surface) may include a holder device, such as a bracket with a hook to form a caddy to retain scissors, cleaning supplies, etc. A caddy may instead be, or additionally be, attached to the column.

As an example modality, this invention serves as a caddy to transport and hold operating room instruments and supplies. For example, personnel may remove an instrument from a bag or pouch on the side of this invention, use it, and re-insert it in the same or other pouch or bag, all the while recording its location on the display area (such as a dry erase board or electronic display). Instruments may be place on a flat area serving as a table (and in a common modality having raised edges), that area optionally being illuminated by a light sourced appropriately mounted on or near the flat area.

The common use of the subject surgical station is in surgical rooms but such use is not so restricted, as the functionality fulfills similar needs in other environments, such as in technical assembly rooms, shops, and clean rooms.

In operation, a user organizes the objects to be used an environment by distributing them among the containers mounted on the vertical sides or surface of the surgical station. Optionally, the information may be recorded or posted on the display area directly above a flat surface, or platform, serving as a table. The display is adapted to be used to record any information, or be used as a means to communicate, in general.

Embodiments—Different ways this invention can look and work—other than what was described above: The above description and uses are what one can expect to see normally in this invention, but there may be variations, which are presently described. That is, any materials or any dimensions may be involved in any configuration, as long as the central function is preserved, placing, storing, and using objects while accounting for and displaying their status in a prominent area atop the invention. The horizontal surface acting as a table may have raised edges so as to discourage objects from sliding from the surface onto the floor.

The "containers" in which objects may be kept may be affixed or mounted below the level of the table and not just on the side (rationale being that when someone utilizes the table top, they do not come in contact with pockets that may contain bodily fluid saturated sponge. Preferably, at least one side located parallel to the front of the display board is provided without any object affixed or mounted thereon so as to avoid any contact of surgical items and the user as he/she writes on, uses or reads the display board. Also, this configuration would avoid potential dangers of having an unprotected hook or other hardware. The manner in which the containers are mounted may be in the style of a "Lazy Suzan", the whole assembly of container being rotatable about a central column of this invention. Preferably, the top is non-rotatable and/or a locking mechanism may be provided to prevent rotation. The columns may have an identifier or a distinct divider (rationale: when rotating the columns for counts, mistake is not made by re-counting same column twice). There may be a variability of possible attachments that would hold items, such as a clip-board (rationale: there may be an opportunity to have a sturdy pocket attached behind the dry-erase for holding of the nurse's clip-board). There also may be other attachments to facilitate objectives of the unit that may be discovered from hands-on use.

FIG. 1 is a top plan view of an embodiment of the subject surgical item counting station with standard sponge count bags with receptacle pouches secured on the sides of the table, shown generally at 10. The following discussion refers generally to FIG. 1, as well as FIGS. 2a-3 which show views of the embodiment of FIG. 1. Surgical item counting station 10 includes a top plate 2 directly perpendicular to and adjacent to a display screen 1, mounted on an adjustable column 3 adjustable through a base, herein configured as an outer rod support 31, that terminates at feet 6. Top plate 2 is a flat, smooth surface on the horizontal plane forming a table top surface that is adjacent and perpendicular to a display screen mounted 1 on an adjustable column 3, which in turn is adjustably mounted on the base, herein outer rod support 31. The surgical station rod, base and feet are similar in construct and size to an IV pole. Top plate 2 has a diameter and centerline c so that top plate 2 is centered in relation to column 3 and rod support 31. Top plate 2 is directly perpendicular to and adjacent to display screen 1 with enough distance v, which is height adjustable, located between the bottom of display screen 1 and top plate 2 to provide space for various surgical tools, items, medicine bottles, container, etc. (See FIG. 2a). Display screen 1 is provided for use in recording the status of objects or for general communication and is a communication board which may be an erasable white board, board holding a paper or paper tablet, an electronic display operable with a key pad and/or operable with voice recognition technology, and/or a touch screen display. Alternatively, display screen 1 may be a tablet device that is mounted on adjustable column 3. Preferably, a mounting bracket 3' is affixed on adjustable column 3 for securing display screen 1. (See FIG. 2b).

Top plate 2 is provided as a flat non-porous linear surface on the horizontal plane which is adapted for the placement of objects, serving as a table top. Top plate 2 may be composed of a glass or transparent polymeric material and a light source (not shown) may be provided under top plate 2 for the transmission of light through top plate 2. The light source may be a lamp that is capable of being clamped onto adjustable column 3 or base, as shown herein as rod support 31, at a location under top plate 2.

Top plate 2 may be capable of rotation. Preferably, however top plate 2 is stationary inasmuch as it has been found that rotation of top plate 2 causes items placed thereon to fall over or roll and become disorderly. What is more, rotation of top plate 2 can cause items to fall over if the item is ≥ in height than the distance v between top plate 2 and the bottom of display screen 1. Thus, it has been found that rotation of top plate 2 poses potential issues and it is preferably that top plate 2 is non-rotatable.

Figure 5:
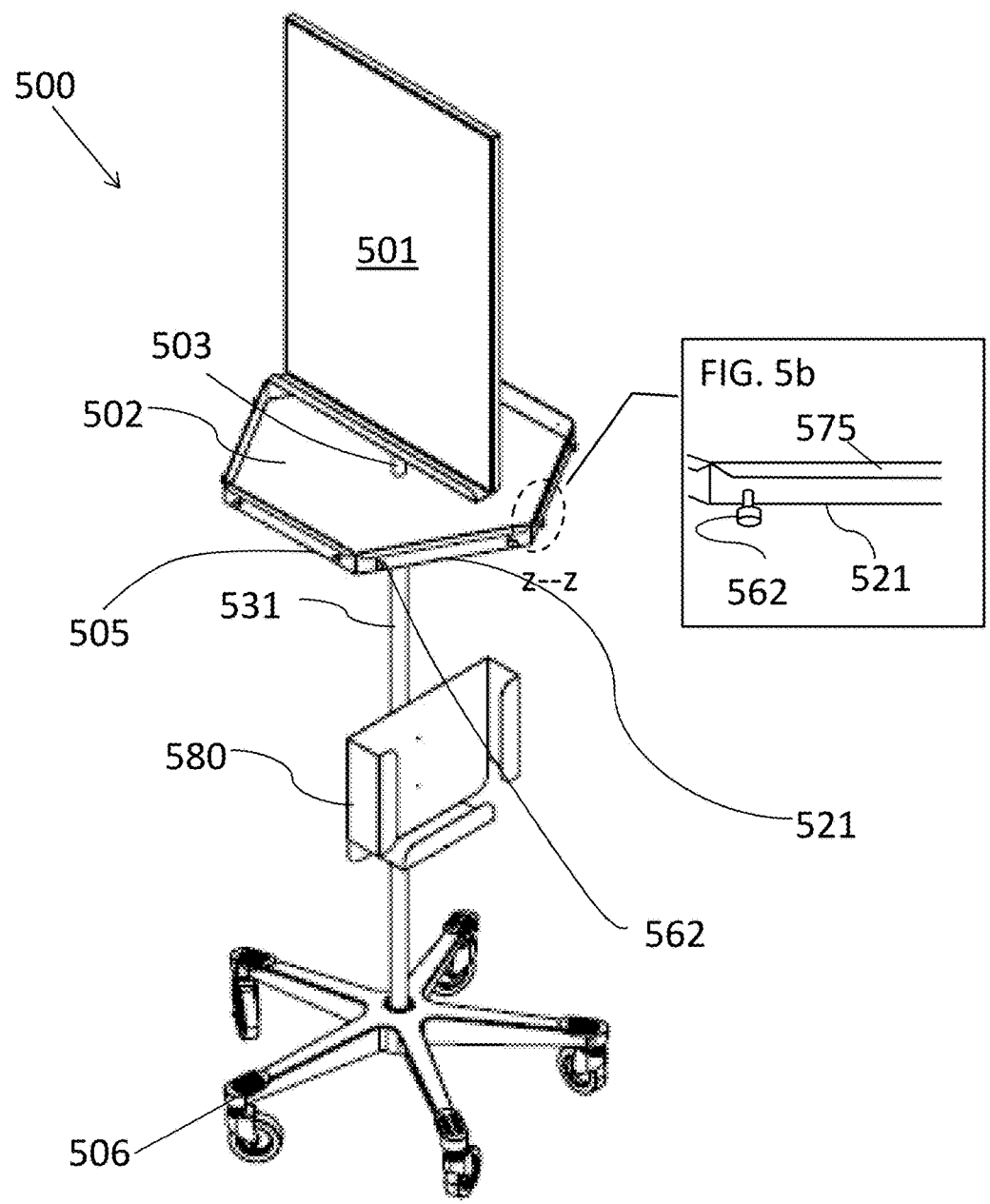
FIG. 5a is a top plan view of an embodiment of the subject surgical item counting station.
FIG. 5b is a cross-sectional exploded view taken along z-z showing an embodiment with an outer top surface rim and the attachment means for attaching a standard sponge count bag.

Table or top plate 2 may be of any geometric shape, but is compact in nature; this one is shown as circular. Preferably, the geometric shape is a hexagon shape having six (6) substantially flat sides (see for example, FIGS. 5-10). Preferably top plate 2 may include a downward extending edges forming a rim (not shown in this FIG.; See FIGS. 5-10, particularly FIG. 5a).

Top plate 2 is located above and is aligned at centerline c with a shelf 5 having a substantially equal diameter to top plate 2 and being located below and in parallel to the top plate. Preferably, shelf 5 has a diameter equal to or slightly less than top plate 2. Preferably, shelf 5 is rotational while top plate 2 is non-rotational. This rotation may be provided as an upside down "lazy Susan" construct (discussed in more detail in FIG. 4). Shelf 5 includes shelf side walls 21 with a mounting means 52 adapted for mounting at least one container device below the top plate 2, herein shown as standard sponge count bags 4. Preferably, top plate 2 and shelf 5 are shaped as hexagons and there are five sponge count bags attached with one side wall remaining clear of a count bag. It is noted that top plate 2 and shelf 5 are herein shown and discussed as separate portions; however top plate 2 and shelf 5 may be integrated together and formed as a single portion.

Shelf 5 may be constructed as a disc or plate, or may be construction as a ring structure. In the embodiment shown, shelf 5 is provided with an side walls 21 with an edge 51 adapted to receive hooks 52 appointed to engage with and mount containers to the side walls of surgical station. Standard sponge count bags 4 are adapted to be mounted on surgical station and are appointed to receive objects, such as surgical sponges or needles, etc., within pockets or pouches 40. Containers/count bags 4 may be affixed in a manner similar to that of a shoe caddy. Container sheets/count bags 4 are preferably mounted by way of apertures 41 located on a top portion of the container sheets/count bags 4 adapted to receive hooks 52 for mounting on shelf 5 parallel and directly adjacent to top plate 2. Feet 6, on which this invention are mounted, preferably are provided with wheels, although these are not mandatory, and preferably feet 6 do not extend past top plate 2 and shelf 5.

One may note that the hanging containers/count bags 4 may be the vertical "wall", the option being a solid surface as a wall directly behind these containers. If there is no solid vertical wall, then there is framework sufficient to support the flat surface acting as a table and the display screen 1 mounted on the surface of table/top plate 2. Though six count bags 4 are shown mounted on shelf 5, it is understood that the number of containers/count bags 4 mounted on the count station is directly proportional to the number of side walls and/or width of the side walls in relation to the count bags 4, of shelf 5.

Figure 2A:
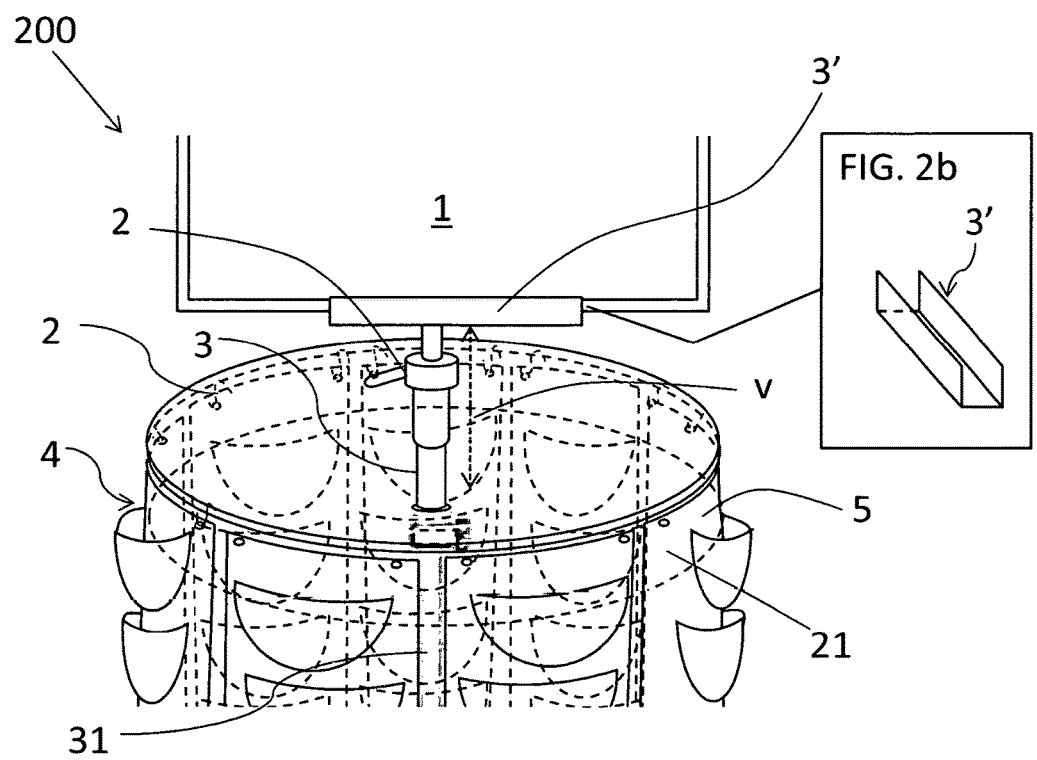
FIG. 2a is a cross-sectional view of the surgical item counting station of FIG. 1.

FIG. 2a is a cross-sectional view of the surgical item counting station of FIG. 1, shown generally at 200. FIG. 2b is a cross-section view of the mounting bracket of FIG. 2a. FIG. 2a represents a close-up side view emphasizing that the column 3 supporting the display screen 1 is adjustable. In this modality, column 3 arises up from the center of the table extending from base or outer rod support 31. The adjustment mechanism may be of any design, such as a compression fitting, set screw, or any other hardware that can allow for changing the height of and holding the display screen in place while in use. Adjustable column 3 is preferably achieved via adjustment apertures along column 3 that when engaged within an outer rod 31 having a slightly larger circumference a locking mechanism 33 locks column 3 in place. Locking mechanism 33 preferably includes a spring loaded knob (or screw knob) with a pin that is adapted to insert within an aligned adjustment aperture of column 3 to lock it in place at a given height or location.

FIG. 3 is a front view of the surgical table of FIG. 1 wherein the standard sponge count bags are not secured on the surgical table, shown generally at 300. FIG. 3 represents a side view of the subject invention, wherein the containers/count bags 4 are removed from the surgical station. A lower shelf or bracket 301 is preferably provided adapted to house unused containers 4 or other supplies for use with the surgical station.

Figure 4:
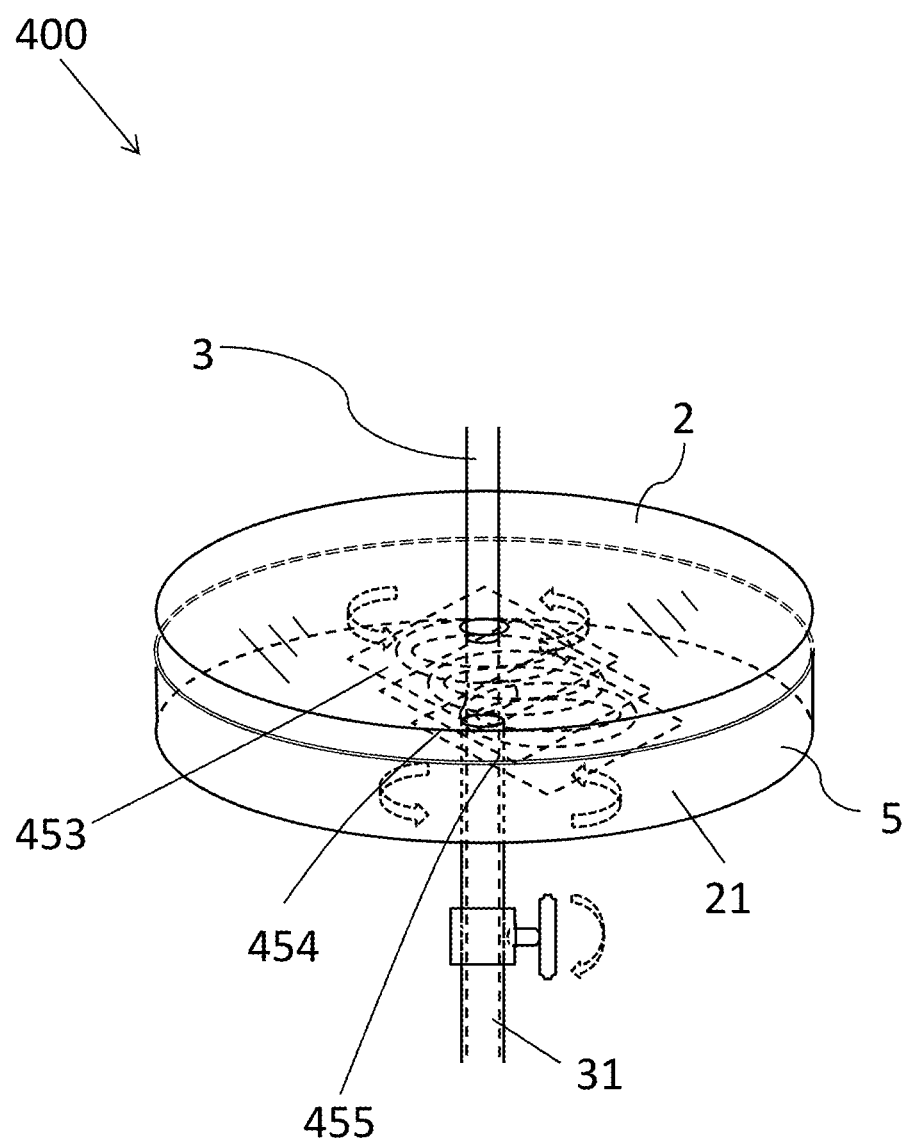
FIG. 4 is a cross-sectional view of the surgical table of FIG. 1 showing an arrangement of the table top of FIG. 1.

FIG. 4 is a cross-sectional view of the surgical table of FIG. 1 showing an arrangement of the table top 2 and shelf 5 of FIG. 1, shown generally at 400. In the embodiment shown, top plate 2 is mounted above shelf 5 which rotational. Shelf 5 is shown shaped as a disc or plate structure provided with an edge 50' adapted to receive hooks appointed to engage with and mount containers/bags (not shown mounted in this figure) to the side walls of surgical station as discussed hereinabove. In the embodiment shown, the arrangement of top plate 2 and shelf 5 rotation of shelf 5 may be achieved for example by way of rotation along column 3 and/support rod 31. Preferably, rotation of shelf 5 is achieved through use of an upside-down "lazy Susan" arrangement. That is, wherein top plate 2 is non-rotational it is fixed to adjustable column 3 and a first collar 453 which is preferably a lazy Susan collar with bearings. A mating second collar 455 faces first collar 453. Collars 453 and 455 have central apertures for passages of column 3 and/or support rod 31 there through. Shelf 5 is affixed to the other side of the second collar 455 so that shelf 455 rotates and access to each of the sleeves/container/count bags 4 is readily achieved by simply rotating shelf 5 while the surgical station itself and the top plate 2 remains still/fixed or non-rotational.

Figure 6:
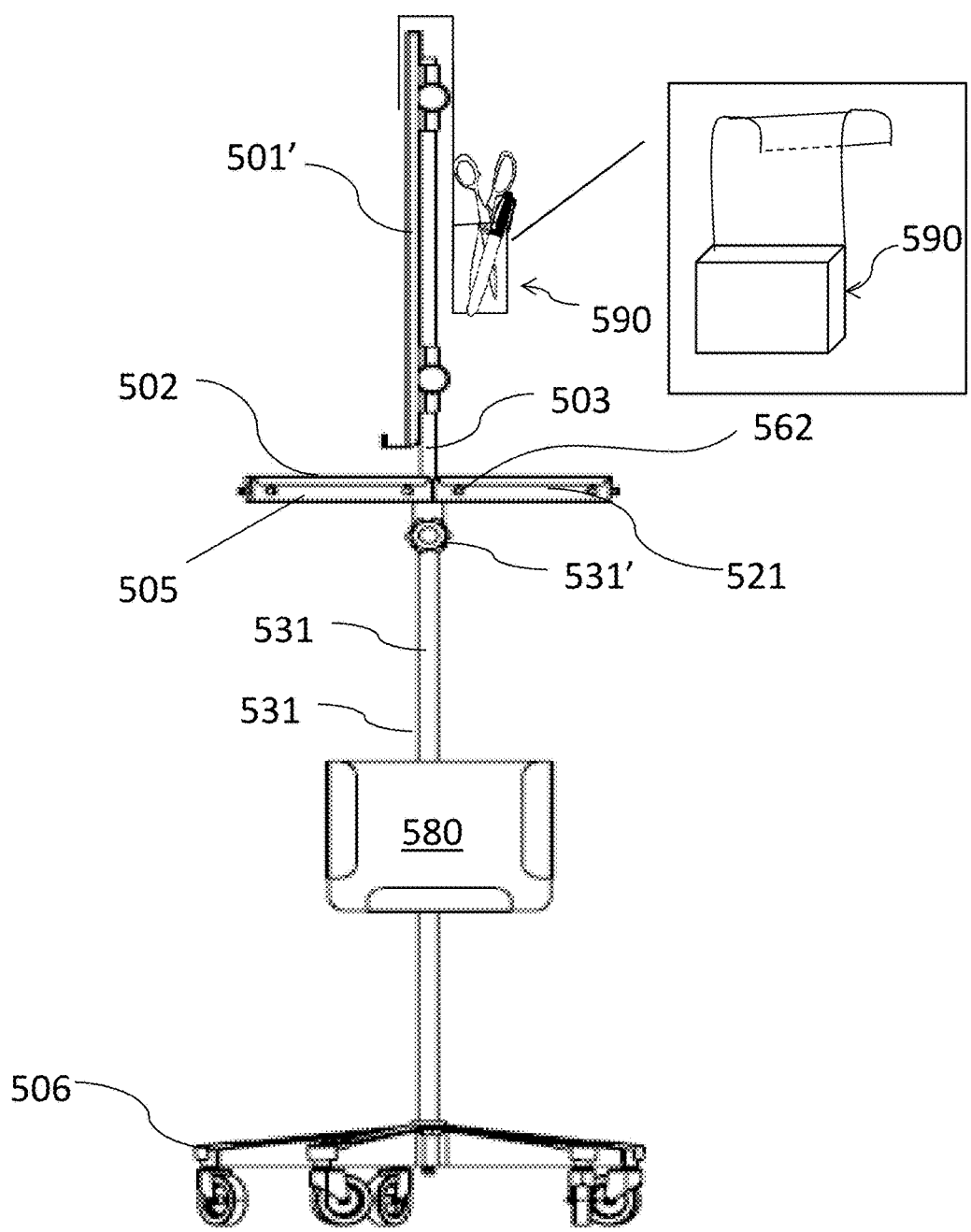
Figure 7:
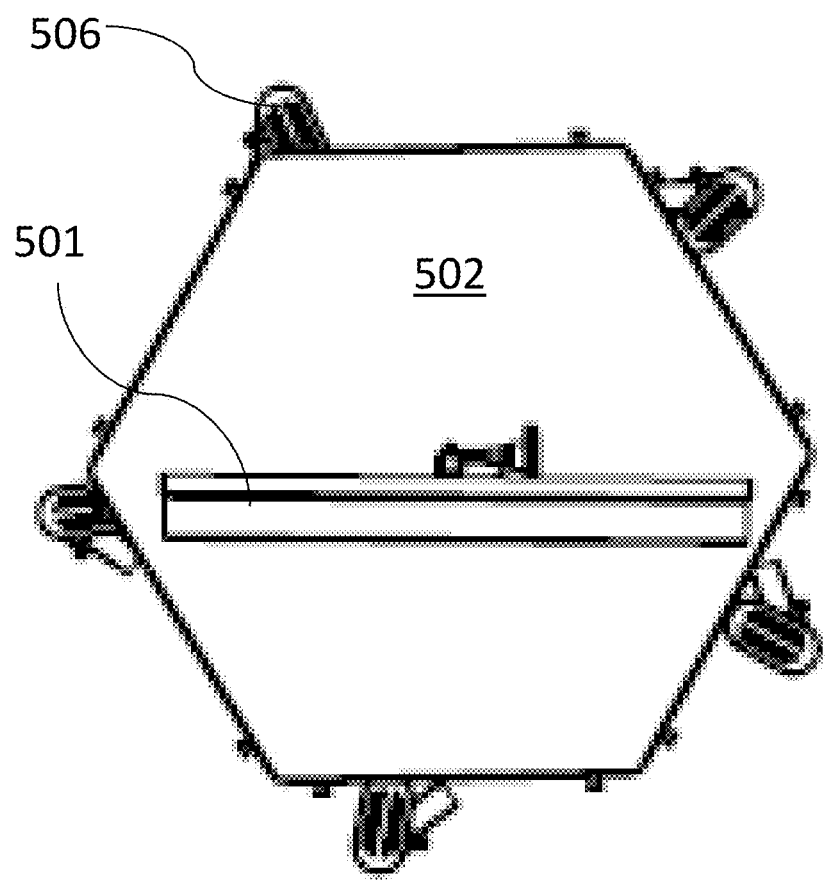
Figure 8:
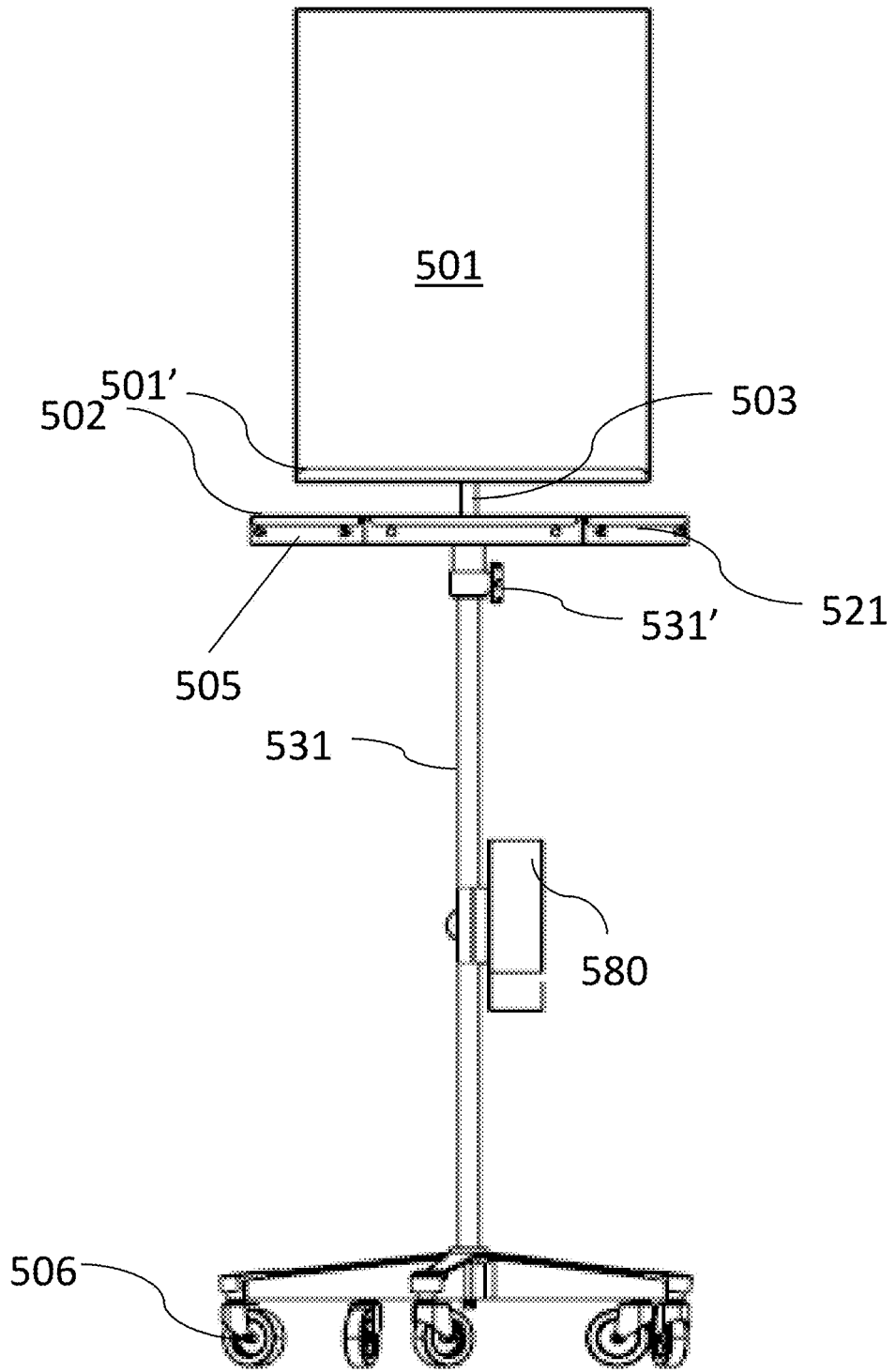
Figure 9:
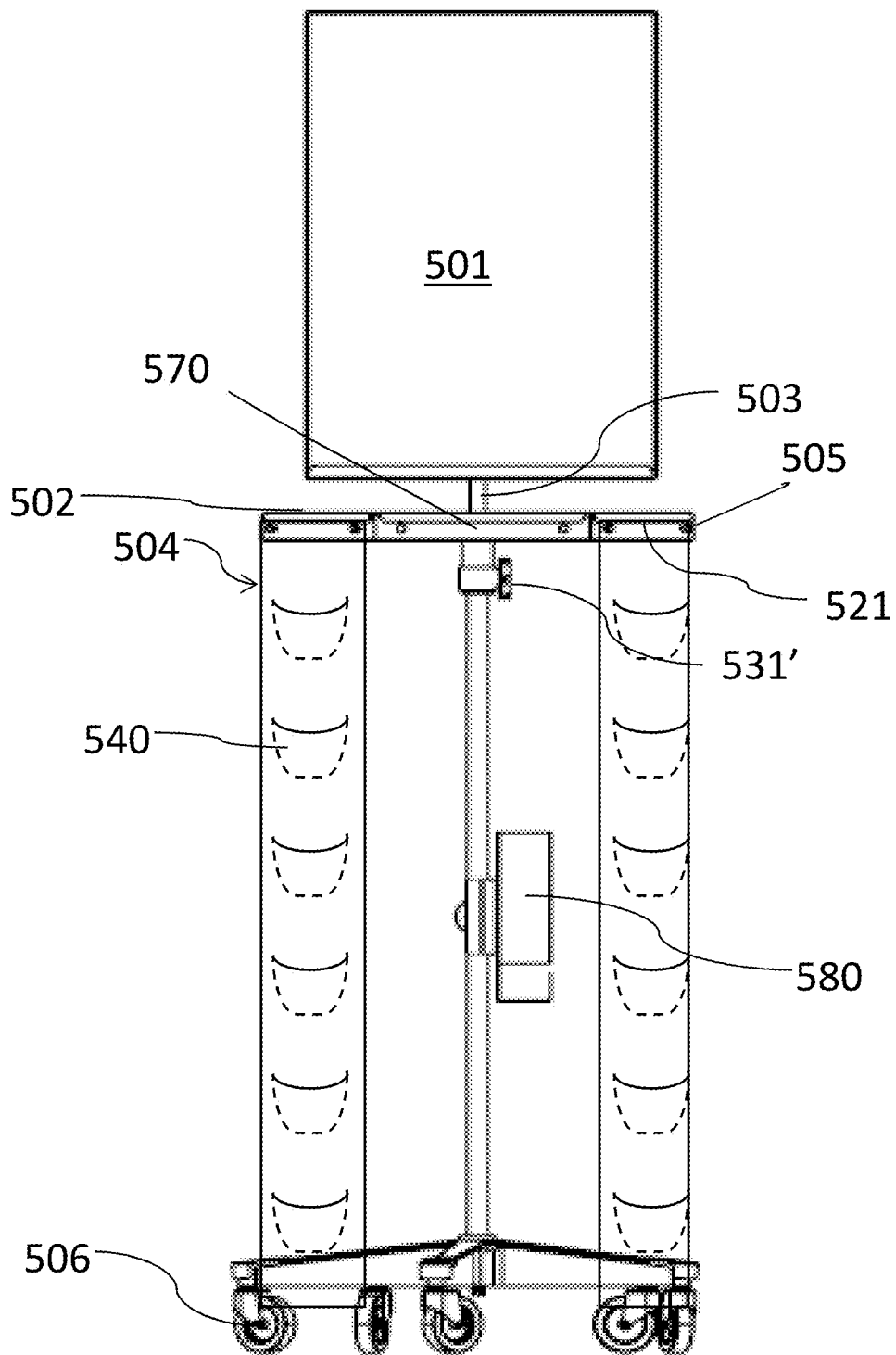
FIG. 9 shows a front view of the surgical item counting station of FIG. 5a with standard sponge count bags mounted on the surgical item counting station.
Figure 10:
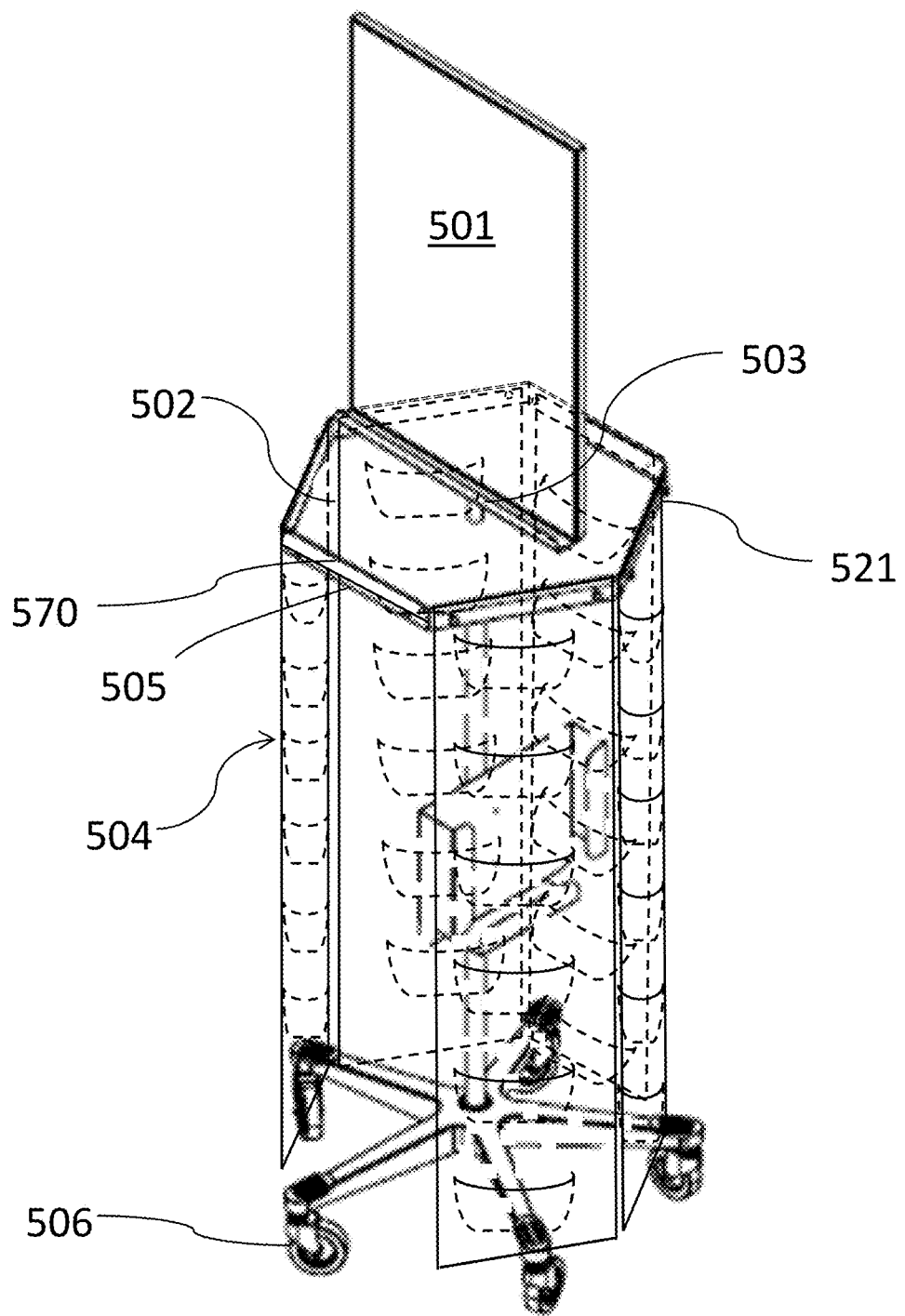
FIG. 10 shows a top plan view of the surgical item counting station of FIG. 5a with standard sponge count bags mounted on the surgical item counting station.

FIG. 5a is a top plan view of an embodiment of the subject surgical item counting station, shown generally at 500. FIG. 5b which shows is a cross-sectional exploded view taken along z-z of FIG. 5a. FIG. 6 shows a side view of the surgical item counting station of FIG. 5a. FIG. 7 shows a top view of the surgical item counting station of FIG. 5a. FIG. 8 shows a front view of the surgical item counting station of FIG. 5a. FIG. 9 shows a front view of the surgical item counting station of FIG. 5a with standard sponge count bags mounted on the surgical item counting station. FIG. 10 shows a top plan view of the surgical item counting station of FIG. 5a with standard sponge count bags mounted on the surgical item counting station.

Referring to FIGS. 5a-10, the surgical item counting station includes a top plate 502 directly perpendicular to and adjacent to a display screen 501, mounted on an adjustable column 503 adjustable through an outer rod support 531 that terminate at feet 506. Top plate 502 is directly perpendicular to and adjacent to a display screen 501 with enough distance located between the bottom of display screen 501 and top plate 502 to provide space for various surgical tools, items, medicine bottles, container, etc. Display screen 501 is provided for use in recording the status of objects or for general communication and is a communication board which may be an erasable white board, board holding a paper or paper tablet, an electronic display operable with a key pad and/or operable with voice recognition technology, and/or a touch screen display.

Top plate 502 is herein shaped as a hexagon which has been found to be a preferred structure to provide a small footprint in the operating room while also providing efficient placement of commercially available sponge container sleeves or rolls. Top plate 502 is provided as a flat non-porous linear surface on the horizontal plane which is adapted for the placement of objects, serving as a table top. Top plate 502 is preferably non-rotational/stationary inasmuch as it has been found that rotation of top plate 502 causes items placed thereon to fall over or roll and become disorderly.

Top plate 502 is located above and is aligned at a centerline with a shelf 505 having the same shape and substantially equal diameter to top plate 502 and being located below and in parallel to the top plate 2. Preferably, shelf 505 has a diameter equal to or slightly less than top plate 502. Preferably, shelf 505 is rotational while top plate 502 is non-rotational. This rotation may be provided as an upside down "lazy Susan" construct (See FIG. 4 and related discussion). Shelf 505 includes shelf side walls 521 with a mounting means 552 adapted for mounting at least one container device below the top plate 504, herein shown as standard sponge count bags 504. Preferably, top plate 502 and shelf 505 are shaped as hexagons as shown, and there are five sponge count bags 504 attached with one side wall 570 remaining clear of a count bag so that the user can rotate shelf 505 to the clear side wall 570 when writing on the display board 501. Wherein shelf 505 is non-rotational the clear side wall 570 is located in line with the display board 501. It is noted that top plate 502 and shelf 505 are herein shown and discussed as separate portions; however top plate 502 and shelf 505 may be integrated together and formed as a single portion, though this is not optimal inasmuch as it is desired that shelf 505 be rotational while top plate 502 remain non-rotational. The clear open space side wall 570 allow the user to avoid coming into contact with dirty sponges, needles or items house within the pouches 540 of the container/count bags 504 and the user has access to a shelve/frame/bracket 580 located on the frame of the device.

Vertically hanging containers/count bags 504 form the vertical "wall" of the station, the option being a solid surface as a wall directly behind these containers.

As best illustrated in FIG. 5b which shows is a cross-sectional exploded view taken along z-z of FIG. 5a, top plate 502 is mounted on shelf 505 which has downward extending shallow side walls 521 perpendicular to contiguously adjoining and extending along substantially the entire perimeter of shelf 505 and includes attachment/mounting means, herein shown as push button pins 562 or hooks located on an outer side 561 of the side walls 521. Pins 562 are appointed to engage with and mount containers/bags 504 to the side walls 521 of shelf 505. Containers, herein shown as standard sponge count bags 504 (see FIGS. 9 and 10) are adapted to be mounted on the surgical station and are appointed to receive objects, such as surgical sponges or needles, etc., within pockets or pouches 540. Container sheets/count bags 504 are preferably mounted by way of apertures located on a top portion of the container sheets/count bags 504 adapted to receive pins 562 for mounting parallel and directly adjacent on shallow side walls 521 of shelf 505. Feet 606, on which this invention are mounted, preferably are provided with wheels, although these are not mandatory. Top plate 502 may include a downwardly extending shallow lip or rim 575 formed at an acute angle (<90°) from the horizontal plane of top plate 502.

As best illustrated in FIG. 6, the surgical item counting station's top plate 502 is shown directly perpendicular to and adjacent to screen support bracket 501' adapted to hold display screen 501, mounted on adjustable column 503 with locking knob 531' adjustable through outer rod support 531 that terminate at feet 506. Display screen 501 is shown secured onto adjustable column 503 by way of bracket support 581. Shelve 580 (or bracket) is provided for holding unused items, such as unused container sheets which can be pulled out and mounted on the surgical station. Additionally, the back of the display board 501 (i.e. opposite from the face of the display board or writing surface) may include a holder device 590, such as a bracket with a hook to form a caddy to retain scissors, cleaning supplies, etc. A caddy may instead be, or additionally be, attached to the column.

Figure 11:
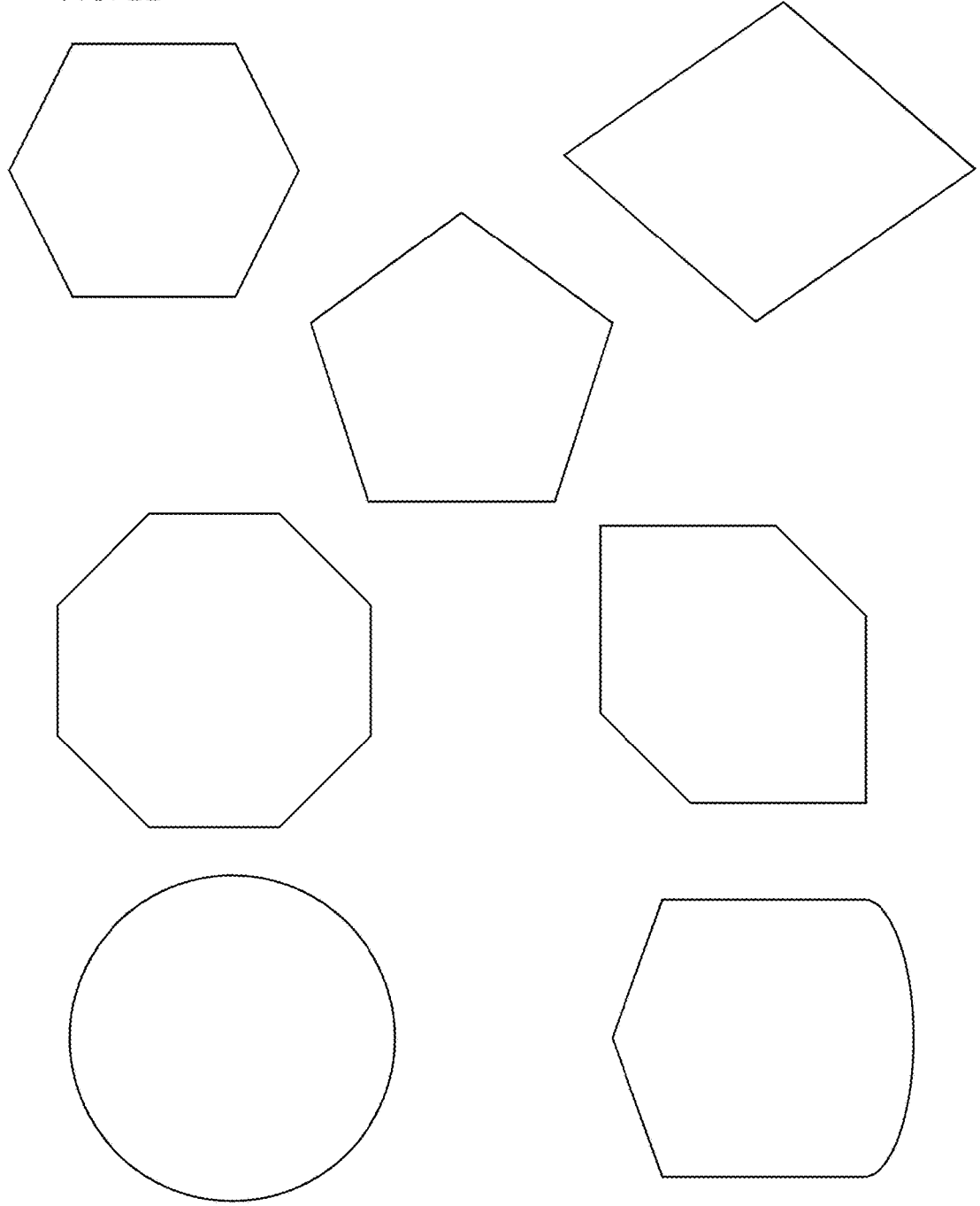
FIG. 11 shows various configurations of the surgical item counting station.

FIG. 11 shows various configurations of the surgical item counting station showing different configurations of the top plate.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A surgical item counting station, comprising:
   a. a top plate having a diameter forming a table top surface and being adjacent and perpendicular to a display screen mounted on an adjustable column mounted on a base terminating at feet, the top plate having a centerline c extending centrally through the top plate, column and base along a vertical plane;
   b. wherein the display screen is adapted to receive and display information about at least one item and general communications;
   c. a rotational shelf having a substantially equal diameter to the top plate and being located below and parallel to the top plate, the rotational shelf having shelf side walls with a mounting means adapted for mounting at least one container device below the top plate, the centerline c extending centrally through the rotational shelf, the top plate being aligned at the centerline c with the shelf along the vertical plane;
   d. the rotational shelf being rotational on a horizontal plane around the column, and wherein the rotation of the shelf causes said container device to also rotate.

2. The surgical item counting station as recited by claim 1, wherein at least a portion of the table top surface of the top plate comprises a magnet surface.

3. The surgical item counting station as recited by claim 1, wherein the top plate comprises a downward extending rim that is at an acute angle downward from the top plate.

4. The surgical item counting station as recited by claim 1, wherein the mounting means of the rotational shelf comprises a hook.

5. The surgical item counting station as recited by claim 1, wherein the mounting means of the rotational shelf comprises a pin with a head structure adapted to be received within an aperture of the container device.

6. The surgical item counting station as recited by claim 1, wherein the top plate remains fixed and does not rotate.

7. The surgical item counting station as recited by claim 1, wherein the top plate is capable of rotating on a horizontal plane.

8. The surgical item counting station as recited by claim 1, wherein the container device is a sponge count bag having pockets or pouches therein adapted to receive soiled sponges and other surgical items, and the sponge count bag extends downward from all but one side of the shelf side walls.

9. The surgical item counting station as recited by claim 1, wherein the base comprises an outer rod support that receives the adjustable column so that the adjustable column can move up and down to adjust height of the display screen.

10. The surgical item counting station as recited by claim 1, wherein the display screen is an erasable white board.

11. The surgical item counting station as recited by claim 1, wherein the display screen is an electronic display operable with a key pad and/or operable with voice recognition technology.

12. The surgical item counting station as recited by claim 1, wherein the display screen is a touch screen display.

13. The surgical item counting station as recited by claim 1 comprising a lower shelf or bracket adapted to house unused supplies.

14. A surgical item counting station, comprising:
   a. a top plate having a diameter forming a table top surface and being adjacent and perpendicular to a display screen mounted on an adjustable column mounted on a base terminating at feet, the top plate having a centerline c extending centrally through the top plate, display screen, column and base along a vertical plane;
   b. wherein the display screen is adapted to receive and display information about at least one item and general communications;
   c. a rotational shelf having a substantially equal diameter to the top plate and being located below and in parallel to the top plate, the rotational shelf having shelf side walls with a mounting means adapted for mounting at least one container device below the top plate, the centerline c extending centrally through the rotational shelf, the top plate being aligned at the centerline c with the shelf along the vertical plane; and
   d. the rotational shelf being rotational on a horizontal plane around the column with the top plate being non-rotational, and wherein the rotation of the shelf causes the container device to also rotate.

15. A surgical item counting station, comprising:
   a. a top plate forming a table top surface and being adjacent and perpendicular to a display screen mounted on an adjustable column mounted on a base terminating at feet, the top plate having a centerline c extending centrally through the top plate, column and base along a vertical plane;
   b. wherein the display screen is adapted to receive and display information about at least one item and general communications;
   c. a rotational shelf having a substantially equal size to the top plate and being located below and parallel to the top plate, the rotational shelf having shelf side walls with a mounting means adapted for mounting at least one container device below the top plate, the centerline c extending centrally through the rotational shelf the top plate being aligned at the centerline c with the shelf along the vertical plane;
   e. the rotational shelf being rotational on a horizontal plane around the column, and wherein the rotation of the shelf causes said container device to also rotate;
   f. wherein the top plate and the shelf are a polygon shape.

16. The surgical item counting station as recited by claim 15, wherein the top plate and the shelf are a hexagon shape.

17. The surgical item counting station as recited by claim 16, wherein one of the side walls of the shelf does not include mounting means, and wherein the container device is appointed to be mounted on and extend downward from all but the one side wall so that the one side wall remains clear of the container device.

* * * * *